United States Patent
Do et al.

(10) Patent No.: US 8,821,846 B2
(45) Date of Patent: Sep. 2, 2014

(54) METHOD FOR LENGTHENING KERATIN FIBERS

(75) Inventors: Thi N. Do, West Orange, NJ (US); Christian J. Lee, Parsippany, NJ (US); William E. McNamara, Chester, NY (US); Cliff A. Milow, Massapequa, NY (US); Tao Zheng, New City, NY (US)

(73) Assignee: Avon Products, Inc, New York, NY (US)

( * ) Notice: Subject to any disclaimer, the term of this patent is extended or adjusted under 35 U.S.C. 154(b) by 1989 days.

(21) Appl. No.: 11/634,658

(22) Filed: Dec. 6, 2006

(65) Prior Publication Data

US 2007/0196307 A1   Aug. 23, 2007

Related U.S. Application Data

(60) Provisional application No. 60/755,731, filed on Dec. 30, 2005.

(51) Int. Cl.
| | | |
|---|---|---|
| *A61Q 1/10* | (2006.01) |
| *A61Q 5/00* | (2006.01) |
| *A61K 8/81* | (2006.01) |
| *A61K 8/87* | (2006.01) |
| *A61K 8/88* | (2006.01) |

(52) U.S. Cl.
CPC .. *A61Q 1/10* (2013.01); *A61Q 5/00* (2013.01); *A61K 8/8129* (2013.01); *A61K 8/87* (2013.01); *A61K 8/8176* (2013.01); *A61K 8/8117* (2013.01); *A61K 8/88* (2013.01)
USPC ...................................... 424/70.7; 424/70.11

(58) Field of Classification Search
None
See application file for complete search history.

(56) References Cited

U.S. PATENT DOCUMENTS

| | | | |
|---|---|---|---|
| 5,620,693 A * | 4/1997 | Piot et al. ................. 424/401 |
| 5,750,121 A * | 5/1998 | Rokitowski ............... 424/401 |
| 6,264,933 B1 | 7/2001 | Bodelin et al. |
| 6,656,487 B2 | 12/2003 | Afriat et al. |
| 6,716,419 B2 | 4/2004 | Zoltowski et al. |
| 6,726,917 B2 | 4/2004 | Kanji et al. |
| 8,586,016 B2 * | 11/2013 | Atis et al. ................. 424/70.7 |
| 2002/0168335 A1 | 11/2002 | Collin |
| 2005/0061349 A1 | 3/2005 | Patel et al. |
| 2005/0191262 A1 | 9/2005 | De La Poterie et al. |

FOREIGN PATENT DOCUMENTS

| | | |
|---|---|---|
| EP | 1208836 A2 | 5/2002 |
| WO | 02/30368 A2 | 4/2002 |
| WO | WO 02/30368  * | 4/2002 |
| WO | 02/49586 A2 | 6/2002 |
| WO | 2004/009043 A1 | 1/2004 |

OTHER PUBLICATIONS

International Search Report dated Nov. 7, 2007 for the corresponding International Patent Application No. PCT/US06/46595.

* cited by examiner

*Primary Examiner* — Jyothsna Venkat

(74) *Attorney, Agent, or Firm* — David M. Joyal; Joan M. McGillycuddy

(57) ABSTRACT

There is a method for lengthening keratin fibers. The method has the steps of a) applying to the keratin fibers a composition having a solvent and one or more polymers soluble or solubilizable in the solvent b) allowing the solvent to evaporate. The composition is applied in an amount sufficient to lengthen the keratin fibers. There are also other methods for lengthening keratin fibers. There is also a mascara composition.

19 Claims, 2 Drawing Sheets

US 8,821,846 B2

METHOD FOR LENGTHENING KERATIN FIBERS

BACKGROUND OF THE INVENTION

1. Field of the Invention

The present invention relates to a method for lengthening keratin fibers of the scalp, eyebrows or eyelashes.

2. Description of the Related Art

Mascara compositions are commonly employed by women to highlight and enhance the appearance of eyelashes. Such enhancements may include the impartation of color or tone, volume, i.e., thickness and length, and curl. Volume and length have been enhanced by the inclusion of fibers in the mascara compositions. For instance, U.S. Pat. No. 6,726,917 discloses a volumizing and lengthening mascara composition having fibers, pigments, and a water-soluble and an oil-soluble film formers. U.S. Pat. No. 6,656,487 discloses a composition having fibers and a copolymer having carboxylate groups and polydimethylsiloxane groups. However, since the size of fibers that can be incorporated into a mascara composition has practical limits, the benefit to be obtained by incorporating fibers is also limited.

One means employed in the art to lengthen eyelashes to a considerable degree is to apply false eyelashes, which are applied by attaching fibers to the base of the eyelashes with an adhesive. Use of false eyelashes can be cumbersome and/or require professional application.

Another means employed in the art to lengthen eyelashes is to build length through multiple applications of a single composition or multiple sequential applications of two or more different compositions.

In the first technique, a formulation of one composition (hereinafter referred to as "single composition") is applied as a single layer and left to set or dry. Then a second layer of the single composition is applied over the single layer. The second layer adds incremental length beyond that of the first layer. Application of the single composition can be repeated as many times as needed to yield the desired eyelash length. Single compositions are commonly wax-based or polymer-based. PCT Application No. 95/15741 discloses a mixture of waxes to impart properties such as film hardness and adhesion to the eyelash. U.S. Provisional Patent Application No. 20020168335A1 discloses a cosmetic composition having a wax and a polymer.

In the second technique, two different compositions are applied sequentially. In such sequenced systems, the first composition, which is typically clear or white in color, is applied to the eyelash to impart a degree of lengthening and is allowed to set or dry. Once the first composition has set, the second composition, which is typically of a color such as black, brown, or blue, is applied over the primary composition imparting additional length. In European Patent Application 1516612A2, a washable mascara is applied to the eyelashes and followed with application of a waterproof mascara. U.S. Provisional Patent Application No. 20050061349A1 discloses a sequenced system employing a composition having fibers in either a washable or waterproof mascara. Using the aforementioned multiple-application techniques for lengthening eyelashes is time-consuming since the changes in length are incremental and gradual.

It would be desirable to have a method for lengthening keratin fibers, such as those of the scalp, eyebrows, and eyelashes, to a considerable degree. It would be further desirable for such lengthened keratin fibers to last for an extended period of time. A consumer need exists for a fast and effective way to lengthen eyelashes without using false eyelashes or products that rely on multiple-application techniques.

SUMMARY OF THE INVENTION

The present invention provides a composition for application to keratin fibers, such as those of the scalp, eyebrows, and eyelashes.

The present invention also provides a filament forming composition for imparting length to keratin fibers, such as those of the scalp, eyebrows, and eyelashes.

The present invention further provides a method for imparting length to keratin fibers, such as those of the scalp, eyebrows, and eyelashes.

The present invention yet further provides a method for imparting length to keratin fibers for an extended period of time.

According to these and other advantages and lengths of the present invention, there is a method for imparting length to keratin fibers, including eyelashes. The method has the steps of a) applying to the keratin fibers a composition having a solvent and one or more polymers that are soluble or dispersible in the solvent and b) allowing the solvent to evaporate. The one or more polymers are present at about 25 wt % or more based on the weight of the composition. The composition exhibits an oscillatory stress range of about 700 to about 10,000 pascals. The composition is applied in an amount sufficient to impart length to the keratin fibers.

According to these and other advantages and benefits of the present invention, there is another method for lengthening keratin fibers. The method has the step of applying to the keratin fibers a composition having one or more polymers wherein the composition is capable of being drawn as a filament.

According to these and other advantages and benefits of the present invention, there is another method for lengthening keratin fibers. The method has the step of applying to the keratin fibers a composition having an amorphous solid wherein the composition is capable of being drawn as a filament.

According to these and other advantages and benefits of the present invention, there is a mascara composition. The composition has a solvent and one or more polymers soluble or dispersible in the solvent. The one or more polymers are present at an amount sufficient to impart filamentous extensions to the keratin fibers, and allowing the solvent to evaporate.

DETAILED DESCRIPTION OF THE INVENTION

It was surprisingly found that there could be a method for imparting length to keratin fibers, such as hair fibers of the scalp, eyebrows or eyelashes, to a considerable degree. It was further surprisingly found that there could be a method for imparting length to keratin fibers for an extended period of time.

The method of the present invention is directed to application of a composition to keratin fibers, particularly the eyelashes. The composition is filament forming and has the effect of extending the length of keratin fibers, such as existing eyelash hairs. The composition exhibits physical properties such that filaments extend a desired length and thickness. Further, optionally, the composition may impart a curling effect to the keratin fibers (and to the filamentous extensions thereof) upon evaporation of solvent(s) from the composition.

The unique characteristics of the present invention are due to single materials and combinations of materials. Rheological tests may be performed to clearly demonstrate the distinctiveness of the present invention in terms of physical characteristics. The composition exhibits plastic deformation in response to an applied force (the pull of the brush or applicator) resulting in elongation. After deformation, the composition fractures leaving filaments on the ends of the keratin fibers.

The physical behavior of the composition may be characterized through rheometry. Many types of rheological techniques and test approaches may be employed in the characterization of the present invention. Various alternative tests and test modifications can be devised and results reported using one or more of a variety of descriptors and or units by those skilled in the science of rheometry. Accordingly, the following description is one possible rheometric approach wherein the fundamental description is intended to embrace all such alternatives, modifications and variances.

Rheometry generally refers to the experimental techniques used to determine the rheological properties of materials, that is, qualitative and quantitative relationships between deformations and stresses. Forced harmonic oscillation is a dynamic rheometric test in which both stress and strain vary harmonically with time, and both viscous and elastic parameters are derived from the material response. Such tests are carried out in the linear viscoelastic regime, which is characterized by a linear response of dynamic viscosity and elasticity with increasing strain amplitude. Such tests can be carried out by using a typical sinusoidal oscillation experiment. The applied stress and resulting strain wave forms can be described as follows:

$$\sigma = \sigma_0 \cos \omega t$$

$$\gamma = \gamma_0 \cos(\omega t - \delta)$$

where $\sigma_0$ is the stress amplitude;
$\gamma_0$ is the strain amplitude;
$\omega = 2\pi f$ is the angular frequency;
t is time; and
$\delta$ is the phase lag (loss angle).

Figure 1:
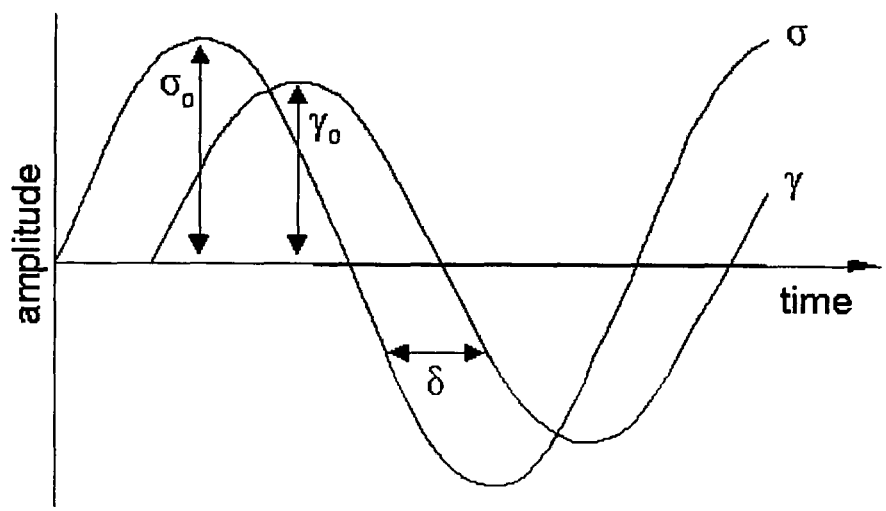
FIG. 1 depicts a plot diagram of sinusoidal wave forms for stress and strain functions.

The sinusoidal wave forms for stress and strain functions are illustrated in FIG. 1. The phase lag and amplitude ratio $(\sigma_0/\gamma_0)$ will generally vary with frequency, but are considered material properties under linear viscoelastic conditions. For an ideal solid, $\delta=0°$, and the response is purely elastic, whereas a Newtonian fluid yields a purely viscous response, $\delta=90°$.

The material functions can be described in terms of complex variables having both real and imaginary parts. Thus, using the relationship:

$$\cos x + j \sin x = e^{jx}$$

where $j=\sqrt{-1}$

Then the stress and strain can be expressed as follows:

$$\sigma = \mathfrak{R}(\sigma_0 e^{j\omega t})$$

$$\gamma = \mathfrak{R}(\gamma_0 e^{j(\omega t - \delta)}) = \mathfrak{R}(\gamma_0 e^{-j\delta} e^{j\omega t})$$

where $(\gamma_0 e^{-j\delta})$ is termed the complex strain amplitude. The shear storage modulus (or storage modulus, for short), which represents the in-phase (elastic) component of oscillatory flow, is defined as follows:

$$G' = \text{storage modulus} = \frac{\sigma_0}{\gamma_0} \cos \delta$$

where G' is the stress in phase with the strain in a sinusoidal shear deformation divided by the strain; it is a measure of the energy stored and recovered per cycle.

The out-of-phase (viscous) component is termed the shear loss modulus (or loss modulus, for short):

$$G'' = \text{loss modulus} = \frac{\sigma_0}{\gamma_0} \sin \delta$$

where G" is the stress 90° out of phase with the strain divided by the strain. It is a measure of the energy dissipated or lost.

The complex dynamic shear modulus, G*, is then defined as follows:

$$G^* = \frac{\text{complex stress amplitude}}{\text{complex strain amplitude}} = \frac{\sigma_0}{\gamma_0} \cos \delta + \frac{\sigma_0}{\gamma_0} j \sin \delta$$

$$G^* = G' + jG''$$

$$\tan \delta = G''/G'$$

Figure 2:
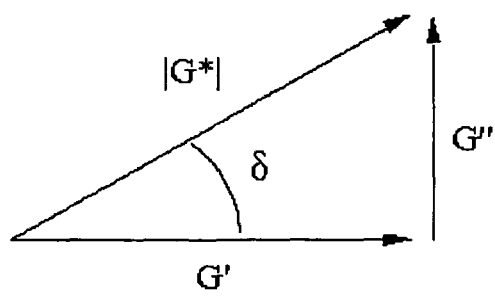
FIG. 2 depicts a vector representation of the function $G''/G'$.

The function G"/G' measures the relative importance of viscous to elastic contributions for a material at a given frequency. A vector representation of the moduli is illustrated in FIG. 2.

The point at which G' and G" intersect and result in a distinct, rapid and sustained decrease in G' and G" is known as the loss tangent or tan $\delta$, which is G"/G'. The loss tangent is a measure of the ratio of energy lost to energy stored in a cyclic deformation. This is the point at which a material is said to have lost its elastic behavior.

The cosmetic composition exhibits an elastic profile that may be defined within the stress and strain relationship as an oscillatory stress range reported in pascals. In concentrated particle suspensions, oscillatory stress can encourage disorder to ordered transition at a measurable yield point. Under oscillatory shear strain, the cosmetic composition can sustain surprisingly large strains compared to compositions of the prior art. When tested at 25° C., using a standard 40 mm, 2° steel cone, at an angular frequency of 10 rad/sec, the composition of the present invention exhibits particle orientation or enters an ordered state within the oscillatory stress range from about 500 pascals to about 10,000 pascals, preferably about 800 pascals to about 5000 pascals, and most preferably about 900 pascals to about 2500 pascals. Prior art compositions under the same test conditions routinely become ordered below 500 pascals.

While not wishing to be bound by any theory, elastic behavior in these ranges may enable the composition to extend in filament form for an average length within a desired minimum and maximum range. The composition exhibits a degree of plasticity sufficient to enable the composition to extend into a filament when pulled to provide a minimum length yet ultimately break or yield at a maximum length.

Upon breakage, the filament experiences less elastic recovery than compositions of the prior art but instead exhibits a degree of plastic deformation in response to an applied force resulting in an instantaneous and non-reversible elongation.

The present invention may be configured as mascara such that the filamentous extension stretch or elongate to a predetermined length, with a known fracture point, such that the filament breaks autonomously and remains anchored to the keratinous fiber and in the elongated state. The filament is in a semi-set condition at the time of breakage and completely sets over time as the solvent evaporates. Furthermore, a mascara composition may be formulated such that the filaments may be drawn out to the desired length by the applicator and held at a desired point for a period of time so as to allow said filament to set. Subsequent movement of the applicator after the set point would then result in filament fracture or breakage at the point of applicator/composition union. The composition can be formulated to yield the desired degree of plasticity. Although not intended to be limiting, typical ranges of filament extension are up to 200 mm when the keratinous fibers are hairs of the head and when the keratinous fibers are eyelashes more typically from 0.01 mm to 5 mm.

The composition has one or more polymers capable of being formulated and subsequently drawn into filamentous form. The polymers may be hydrophilic, hydrophobic, or any combination thereof depending on the desired properties of the composition. The polymers may be any known in the art to be safe for use on the skin and the eyelashes. The polymers may optionally be selected from those known to be useful as film formers.

The polymers are present in an amount sufficient to enable the formation of a fluid composition adapted to be drawn into a filament. The polymers are preferably present from about 15 wt % to about 75 wt % based on the total weight of the composition. More preferably, the polymers are present from about 35 wt % to about 45 wt %. Most preferably, the polymers are present from about 25 wt % to about 30 wt %.

The polymer(s) may be of natural or synthetic origin. Suitable hydrophilic polymers include, but not limited to the following, acrylics (acrylates), polyacrylates, acrylamide polymers and copolymers and quaternary salts thereof, urethanes, polyurethanes, polyesters, polysaccharides, polyamides, polyols, polyethers, cellulosics, proteins, polyamino acids, esters derived from rosin, latexes, or any combinations thereof. Suitable hydrophobic polymers include, but not limited to, polyolefins, polyvinylpyrrolidone polymers and copolymers, polyethylenes, polyalkyls, polystyrenes, triglycerides, epoxy resins, shellacs, or any combinations thereof.

The composition can be aqueous or anhydrous. The composition can take any fluid form, such as a solution, suspension, dispersion, or emulsion. An emulsion can be of any conventional type, including oil-in-water, water-in-oil, silicone-in-water, water-in-silicone, wax-in-water, and water-in-wax. The composition typically exhibits the physical consistency of a lotion, cream, or gel. The physical consistency is such that the composition can be easily applied to the keratinous fibers with a brush, comb, or other suitable applicator. In a preferred embodiment, the composition can be applied to the eyelashes as a mascara with a mascara brush.

The composition contains one or more cosmetically acceptable solvents in which the polymer is soluble or dispersible. Water is a preferred solvent in aqueous compositions. Other useful hydrophilic solvents include lower alcohols and polyhydric alcohols. Useful hydrophobic solvents include volatile and non-volatile oils. The term "volatile" means the oil has a measurable vapor pressure, or a vapor pressure of at least 2 mm of mercury at 20° C. The term "non-volatile" means that the oil has a vapor pressure of less than 2 mm of mercury at 20° C. Suitable volatile oils include linear silicones, cyclic silicones, paraffinic hydrocarbons, or mixtures thereof. Various straight or branched chain paraffinic hydrocarbons having 5 to 40 carbon atoms, more preferably 8 to 20 carbon atoms are suitable for use in the present invention. Particularly preferred are $C_8$-$C_{20}$ isoparaffins, such as those disclosed in U.S. Pat. Nos. 3,439,088 and 3,818,105, both of which are incorporated herein by reference. Suitable non-volatile oils may also include naturally occurring glyceryl esters of fatty acids or triglycerides. Examples include lanolin oil, triisocetyl citrate, $C_{10}$-$C_{18}$ triglycerides, coconut oil, corn oil, palm oil, and sunflower seed oil. Suitable oils also include synthetic or semi-synthetic glyceryl esters, e.g. fatty acid mono-, di-, and triglycerides that have been modified. Modified glycerides include, for example, acetylated castor oil, glyceryl stearate, glycerol dioleate, glyceroldistearate, glycerol myristate, PEG castor oils, PEG glycerol oleates, and PEG glycerol stearates. Other suitable non-volatile oils include hydrogenated polyisobutene, squalene, fatty esters, fatty alcohols, petrolatum and mineral oil. The composition may also contain the same substances as cosmetically acceptable vehicles or carriers.

The solvent is present in an amount sufficient to dissolve or disperse the polymer as well as otherwise provide a sufficient degree of fluidity to the composition. The solvent is preferably present from about 10 wt % to about 85 wt %, more preferably present from about 30 wt % to about 50 wt %, and most preferably present from about 25 wt % to about 35 wt %.

The present invention may employ polymers having various glass transition temperatures. By mixing polymers with varying glass transition temperatures, performance properties of a composition can be regulated. Furthermore, plasticizers may be used to modify the glass transition temperatures of the polymers to modify the performance properties of the polymers or the composition as a whole. Plasticizers are additives that soften a material by either softening the final product or to increase the workability of the material before it hardens. Plasticizers work by embedding themselves between polymer chains, thereby increasing spacing or free volume. Thus, glass transition temperature is reduced, which makes the material more pliant. Useful plasticizers include, but are not limited to, the following: fatty alcohols, fatty esters, fatty acid esters, and inorganic acid esters.

Polymer solutions and polymer melts containing thermoset or thermoplastic resins display unique non-Newtonian behavior under shear stress. The rheological characteristics of these polymer systems can be further modified by the addition of particulate fillers of various size (micron to colloidal), shape (spherical to platelet), or composition. The extent of the filler effect is dependent upon the degree of particle dispersion, particle-particle interactions, and particle-polymer interactions. Numerous theories exist in the literature to predict and describe the flow behavior of filled polymeric systems based on filler particle geometries. In the present invention, particles may form a percolative network in a filled polymer system under zero shear conditions, yet readily flow in a predictable manner under applied stress. This behavior, known as thixotropy, is an important characteristic in functional cosmetics where proper application is dependent upon rheological properties. For example, extension of keratin fibers using polymer-based formulations requires a low viscosity for uniform deposition upon initial application and subsequent high viscosity (formation of a rigid gel) upon standing to facilitate a drying/setting processes.

The extent of interaction between the filler and polymer systems can be described in terms of thermodynamics using the works of adhesion and cohesion. Strong polymer-particle interaction, work of adhesion, results in poor network formation, thus reduced thixotropic behavior. Strong particle-particle interaction and/or work of cohesion may result in poor particle dispersion or undesirable rheological behavior. The optimal condition lies between the two extrema where the difference between the work of adhesion and work of cohesion is less than zero. In general, the ideal particles can be selected based on their surface energy (surface chemistry) with respect to characteristics of the polymer system, with respect to each other (mixtures of particles and the Hamaker constant), and their physical shape (i.e. fractal, spherical, platelet, etc).

The cosmetic composition preferably has one or more fillers or particles. Useful fillers and/or particles include any known in the cosmetic art. These materials enhance the settled time and stiffness of the filaments formed. Examples of useful fillers include clays and organic and inorganic powders. The fillers/particles preferably have an aspect ratio (length/width) from about 1 to about 1000, more preferably from about 1 to about 500, and most preferably from about 1 to about 50. The fillers/particles are preferably present from about 20 to about 50 wt %, more preferably present from about 30 to about 45 wt %, and most preferably present from about 25 to about 35 wt % based on the total weight of the cosmetic composition.

The composition preferably has one or more pigments, pearlescents, and/or colorants therein. Useful pigments and/or colorants include any known in the cosmetic art. Coatings and surface treatments on pigments may also enhance the shine or gloss exhibited by mascara compositions. Examples of useful pigments include titanium dioxide, zinc oxide, iron oxide, chromium oxide, ferric blue, and mica; organic pigments include barium, strontium, calcium or aluminum lakes, ultramarines, and carbon black; colorants include D&C Green #3, D&C Yellow #5, and D&C Blue #1. Pigments and/or colorants may be coated or surface treated with one or more compatibilizers to aid in dispersion in either or both of the aqueous or wax phases. When silicone vehicles are used, pigments and/or colorants surface treated with dimethicone copolyol are preferred. Pearlescent agents are understood as meaning iridescent particles, in particular, particles produced by certain mollusks in their shell or synthesized pearlescent particles. Pearlescent agents particularly serve to modify the texture of the composition.

Pigments can be present in the composition in an amount of 1 wt % to about 50 wt % of the total weight of the composition, and preferably in an amount of about 30 wt % to about 45 wt %.

The composition of the invention may further have any ingredient conventionally used in the cosmetic field, in particular in the manufacture of mascara and eyelash products. The amounts of these various ingredients are those conventionally used in the cosmetic field to achieve their intended purpose, and range typically from about 0.01 wt % to about 20 wt % by weight of the composition. The nature of these ingredients and their amounts must be compatible with the production of stable compositions useful in the method of the present invention.

Compositions may also include one or more of the following optional ingredients: amino acids, antioxidants, emollients, emulsifiers, eyelash protectants, eyelashes penetration enhancers, fillers, humectants, moisturizers, preservatives, surfactants, thickeners, vitamins, waxes and any combinations thereof.

The composition may be applied to the eyelashes as often as needed to maintain the desired length. The composition is typically applied to the upper side of the natural hairs with an outward, extending motion (in the general direction of the extension of the hairs) with the filaments forming at the ends of the hairs until the composition breaks or yields terminating such formation. Application results in a coating on at least a portion of the natural hairs in addition to filament formation. The composition then dries through evaporation of solvent and other volatiles. Periodic re-application will be necessary in the normal course as the filamentous extensions of the composition wear off. The filamentous extensions will exhibit a considerable degree of wear-resistance and water-resistance. The filamentous extensions will maintain their integrity for as long as the effect is desired by the consumer.

The composition may alternately be characterized as an amorphous fluid or uniform suspension having one or more filament forming agents that are amorphous solids, preferably selected from the aforementioned polymers. An amorphous solid is a solid in which there is no long-range order of the positions of constituent atoms. Amorphous solids can exist ion two distinct states, the rubbery state and the glassy state.

The following are examples of the present invention. Unless otherwise indicated, all percentages or parts are by weight.

EXAMPLES

Examples and Control

Compositions useful in the method of the present invention can be prepared and tested for filament formation, flexibility, dry times and oscillatory stress compared to that of a prior art composition.

The composition of the control is designated as Sample #1. Sample #1 has the composition shown below in Table 1.

TABLE 1

| Components | Percentage (%) |
|---|---|
| PVP | 12.0 |
| PVA | 18.0 |
| TiO$_2$ | 40.0 |
| Anti-foam | 0.5 |
| preservative | 1.0 |
| water | 28.5 |
| total | 100.0 |

Sample #1 can be prepared by the following method. Combine water, antifoam agent, and TiO$_2$ (titanium dioxide) and mix well with a mixer set at 50 to 100 rpm to form a mixture. Slowly disperse PVA (polyvinylalcohol) in the mixture, and when addition is complete, set temperature to 60° C. to 80° C. During heating, add PVP (polyvinylpyrrolidone) and mix well. Cover the batch and continue mixing and heat for 1 hour or until all polymers dissolve. Cool the solution to 45° C. and add preservative.

Sample #2 has the composition set forth in Table 2 below.

TABLE 2

| Components | Percentage (%) |
|---|---|
| Polyimide (30% in water) | 50.0 |

TABLE 2-continued

| Components | Percentage (%) |
|---|---|
| TiO$_2$ | 48.5 |
| antifoam | 0.5 |
| preservative | 1.0 |
| total | 100.0 |

Sample #2 is prepared by the following method. Combine water, antifoam, preservative and mix with a mixer set at 50 to 500 rpm. During mixing add TiO$_2$. When addition is complete, cover the batch and set the mixer at 100 rpm. After 30 minutes, stop the mixing.

Sample #3 has the composition set forth in Table 3 below.

TABLE 3

| Components | Percentage (%) |
|---|---|
| DynamicX (30% in water) | 50.0 |
| TiO$_2$ | 48.5 |
| Antifoam agent | 0.5 |
| Preservative | 1.0 |
| total | 100.0 |

DynamicX is polyurethane-14AMP-acrylate (National Starch)

Sample #3 is prepared in substantially the same manner as for Sample #2.

Sample #4 has the composition set forth in Table 4.

TABLE 4

| Components | Percentage (%) |
|---|---|
| Koboguard 5400 IDD | 35 |
| Iron Oxide black | 50 |
| Isododecane | 15 |
| total | 100 |

Koboguard 5400IDD is a hydrogenated polycyclopentadiene by Kobo.

Sample #4 is prepared in substantially the same manner as for Sample #2.

All samples are transferred to the appropriate component with the appropriate brush and wiper. Each sample was brushed/applied to the faux eyelashes. As filaments form and achieve the desired length, the brush is held until the solvent is dried off and the filament breaks off from the brush and stays on the eyelashes. The time that filaments break off from the brush is referred to as the set-off time and is recorded in seconds. The number of filaments formed is recorded as the initial number of filaments.

Another test is performed to test for the flexibility of the filaments. After set off, the filament is allowed to dry for one minute. Then, using a clean brush, the filament is brushed through 14 times. The number of remaining filaments is recorded. The higher the number of remaining filaments, the better the sample. Results are set forth below in Table 5.

TABLE 5

|  | Control | Example 1 | Example 2 | Example 3 | Example 4 |
|---|---|---|---|---|---|
| Set-off time (seconds) | 60 | 30 | 20 | 22 | 60 |
| initial number of filament | 0 | 13 | 15 | 9 | 12 |
| number of filaments remaining | 0 | 13 | 7 | 5 | 5 |

All samples are run on the dynamic rheometer at 25° C. using a standard 40 mm, 2° steel cone. The control loses elasticity at approximately 299 pa, while the compositions of the examples experience a loss of elasticity at approximately 1286 pascals (pa). The examples exhibit markedly greater elastic ranges (approximately 4 times) compared to the control. The two compositions of the examples can be drawn into a filament while the control cannot.

It should be understood that the foregoing description is only illustrative of the present invention. Various alternatives and modifications can be devised by those skilled in the art without departing from scope of the invention. Accordingly, the present invention is intended to embrace all such alternatives, modifications and variances that fall within the scope of the appended claims.

What is claimed is:

1. A method for lengthening keratin fibers, comprising
    a) applying to the keratin fibers a fluid composition having
        i) a solvent;
        ii) polymer selected from the group consisting of polyimide, polyurethane-14AMP-acrylate and hydrogenated polycyclopentadiene, and
    b) pulling said fluid composition with a brush or applicator to draw out said composition beyond the end of said keratin fibers; and
    c) allowing said solvent to evaporate such that said polymer set to thereby form a filamentous extension anchored to the keratin fiber;
wherein said composition is free of polyvinyl pyrrolidone and polyvinyl alcohol.

2. The method of claim 1, wherein the keratin fibers are selected from the group consisting of those of the scalp, eyebrows, and eyelashes.

3. The method of claim 1, wherein the fluid composition exhibits particle orientation within the oscillatory stress range of about 500 to about 10,000 pascals.

4. The method of claim 1, wherein the fluid composition exhibits particle orientation within the oscillatory stress range of about 800 to about 5000 pascals.

5. The method of claim 1, wherein the fluid composition exhibits a loss tangent or Tan δ less than one.

6. The method of claim 1, wherein the polymer is present in an amount about 15 wt % to about 75 wt % based on the total weight of the composition.

7. The method of claim 1, wherein the composition further comprises fillers/particles present at about 20 wt % to about 50 wt % based on the total weight of the composition.

8. The method of claim 1, wherein the solvent is present at about 10 wt % to about 85 wt % based on the total weight of the composition.

9. The method of claim 8, wherein the solvent is water.

10. The method of claim 1, further comprising a pigment, colorant, or pearlescent.

11. The method of claim 10, wherein the pigment is titanium dioxide.

12. The method of claim 1, wherein keratin fibers are lengthened an average of up to 20 mm.

13. A method for lengthening eyelashes, comprising
a) applying to the eyelashes a fluid composition having
   i) a solvent;
   ii) polymer selected from the group consisting of polyimide, polyurethane-14AMP-acrylate and hydrogenated polycyclopentadiene;
b) pulling said fluid composition with a brush or applicator to draw out said composition beyond the end of said keratin fibers; and
c) allowing said solvent to evaporate such that said polymer set to thereby form a filamentous extension anchored to the keratin fiber,
wherein the one or more polymers is present in the range from about 10 wt % to about 80 wt % based on the weight of the composition, wherein the composition exhibits particle orientation within an oscillatory stress range of about 500 to about 10,000 pascals;
wherein said composition is free of polyvinyl pyrrolidone and polyvinyl alcohol.

14. The method of claim 13, wherein the fluid composition exhibits particle ordering within an oscillatory stress range of about 800 to about 5000 pascals.

15. The method of claim 13, wherein the polymer is present in an amount about 15 wt % to about 75 wt % based on the total weight of the composition.

16. The method of claim 13, wherein the solvent is present at about 25 wt % or more based on the total weight of the composition.

17. The method of claim 13, wherein the solvent is water.

18. The method of claim 13, further comprising a pigment, colorant, or pearlescent.

19. The method of claim 13, wherein eyelashes are lengthened an average of up to 20 mm.

\* \* \* \* \*